United States Patent
Hettiarachchi et al.

[11] Patent Number: 5,883,311
[45] Date of Patent: Mar. 16, 1999

[54] METHODS AND APPARATUS FOR DETECTION OF CRACK INITIATION

[75] Inventors: Samson Hettiarachchi, Menlo Park; Gary Paul Wozadlo, Los Gatos, both of Calif.

[73] Assignee: General Electric Company, Schenectady, N.Y.

[21] Appl. No.: 667,711

[22] Filed: Jun. 21, 1996

[51] Int. Cl.⁶ .................................................. G01N 19/08
[52] U.S. Cl. .............................................. 73/799; 73/809
[58] Field of Search .............................. 73/794, 795, 796, 73/809, 799

[56] References Cited

U.S. PATENT DOCUMENTS

| | | | |
|---|---|---|---|
| 3,381,526 | 5/1968 | Rastogi et al. | 73/809 |
| 3,427,873 | 2/1969 | Mehdizadeh | 73/809 |
| 4,056,973 | 11/1977 | Prevorsek et al. | 73/809 |
| 4,149,407 | 4/1979 | Strom et al. | 73/794 |
| 4,676,110 | 6/1987 | Hodo et al. | 73/809 |

*Primary Examiner*—George Dombroske
*Assistant Examiner*—Max H. Noori
*Attorney, Agent, or Firm*—Armstrong, Teasdale, Schlafly & Davis

[57] ABSTRACT

Methods and apparatus for detecting the onset of stress corrosion cracking are described. In one aspect, the present invention is a passive detector for in-situ detection of the onset of stress corrosion cracking in a nuclear reactor. The detector includes a ceramic insulator mounting member. A first material sample and a second material sample are secured to the mounting member. In the one embodiment, a metal bolt extends through the first and second material samples and secures the samples to the mounting member. The first material sample is cold worked to induce residual tensile stress and the second material is not cold worked. A first electrical conductor is electrically connected to the first material sample and a second electrical conductor is electrically connected to the second material sample. An electrometer is electrically connected to the first and second electrical conductors, and the electrometer is configured to generate a strain induced differential potential signal representative of a difference in potential between the first sample and the second sample. Alternatively, a strain induced differential current signal can be monitored using a zero resistance ammeter in place of the electrometer. The detector configured to be located within the reactor at the location where monitoring is desired, and during the reactor operation, if transients are observed in the differential signal, this condition indicates that at the location of the detector, an inspection should be performed at the next outage to determine whether cracking is occurring. Active detectors, detection methods, and test apparatus also are described.

15 Claims, 5 Drawing Sheets

METHODS AND APPARATUS FOR DETECTION OF CRACK INITIATION

FIELD OF THE INVENTION

This invention relates generally to materials exposed to environments susceptible to stress corrosion cracking and, more particularly, to detecting the early stages of stress corrosion cracking initiation in nuclear reactor components.

BACKGROUND OF THE INVENTION

The detection of early stages of stress corrosion cracking initiation has been a subject of great interest to the corrosion community, particularly to those in the nuclear industry. Such early detection of cracking would enable one to take corrective action before the occurrence of major component failures. Particularly in a nuclear reactor, it is highly desirable and imperative to prevent major component failure.

The most commonly known stress corrosion cracking detection approach is to use a constant extension rate tensile (CERT) test. In a CERT test, a dog bone type tensile specimen is stressed at a constant extension rate within an autoclave containing the corrosive environment. The test is interrupted at known % strains, and at each interruption, the specimen is examined for crack initiation. The crack initiation process has been studied, using CERT tests, as a function of water temperature, heat treatment temperature, cold work, etc.

Although CERT tests provide very valuable information, a shortcoming of the CERT test technique is the need to periodically remove the specimen from the high temperature autoclave for microscopic examination to detect the initiation of stress corrosion cracks. Removing and inspecting the specimen adds time and expense to the testing operations. In addition, the CERT test approach cannot be used as an in-situ tool for the early detection of stress corrosion cracks in the environment.

It would be desirable to prevent major component failure due to stress corrosion cracking by early detection of the initiation of such cracking. It also would be desirable to provide an in-situ method and device for crack detection in a reactor and other environments.

SUMMARY OF THE INVENTION

These and other objects are attained by an in-situ detector for detecting the onset of stress corrosion cracking in a corrosive environment, such as in a nuclear reactor. In one embodiment, the detector includes a ceramic insulator mounting member, and a first material sample and a second material sample are secured to the mounting member. In the one embodiment, a metal bolt extends through the first and second material samples and secures the samples to the mounting member. The first material sample is cold worked and the second material is not cold worked. The first material sample can be cold worked, for example, by rolling, forging, machining, or by subjecting the sample to a tensile stress.

A first electrical conductor is electrically connected to the first material sample and a second electrical conductor is electrically connected to the second material sample. An electrometer is electrically connected to the first and second electrical conductors, and the electrometer is configured to generate a strain induced differential potential signal representative of a difference in potential between the first sample and the second sample.

To use the above described detector to detect the possible onset of cracking in a reactor, the detector is located within the reactor at the location where monitoring is desired. During the reactor operation, the strain induced differential potential signal is monitored. If the strain induced differential potential signal remains substantially unchanged during reactor operation, then at least at the location of the detector, this condition indicates that no cracking is occurring. If, however, the strain induced differential potential signal changes during reactor operation, e.g., transients are present typical of crack initiation as described hereinafter in more detail, this condition indicates that at the location of the detector, an inspection should be performed at the next outage to determine whether cracking is occurring. This condition also indicates that the location of the detector is a location that should be subjected to close in-vessel visual inspection (IVVI) for cracks.

The above described in-situ detector provides the advantage of facilitating early identification of crack initiation. Such a detector provides this important advantage and without necessarily requiring removal of a material sample and subjecting the sample to inspection. Specifically, with the above described detector, and if no transients are observed in the monitored differential potential signal, there is no detector indication that sample removal and inspection is required, although such removal and inspection may be performed due to other circumstances.

Further, the above described detector is sometimes referred to herein as a passive detector in that no tensile stresses are directly applied to the first material sample during detection operations. The present invention also includes, in another aspect, active detectors in which tensile stresses are directly applied to the first material sample during detection operations.

In yet another aspect, the present invention is an apparatus for testing materials to detect the onset of stress corrosion cracking. For laboratory use, the apparatus includes a straining apparatus and an autoclave. The straining apparatus has a cross head and a pull rod coupled to the cross head. A support plate is positioned within the autoclave, and the support plate is configured to engage a first material sample. The autoclave has a head portion and a substantially cylindrical main body portion. The straining apparatus further includes support rods extending from the autoclave head portion to the support plate. A coupling with an insulated sleeve is provided for coupling the pull rod to the first material sample. A load cell is positioned for sensing the tensile load acting on a first material sample. The autoclave is positioned below the cross head.

The apparatus further includes a first electrical conductor for being electrically connected to the first material sample, and a second electrical conductor for being electrically connected to a second material sample. An electrometer is electrically connected to the first and second electrical conductors, and the electrometer is configured to generate a strain induced differential potential signal representative of a difference in potential between the first sample and the second sample. In one embodiment, a computer is connected to receive the output of the electrometer and the output of the load cell.

In operation, the first material sample is located in the autoclave and connected to and between the straining apparatus insulated coupling and the insulated support plate. One end of the first electrical conductor is secured, e.g., welded, to the first material sample. The second material sample also is located in the autoclave and is supported within the autoclave by the second electrical conductor. Specifically, the second electrical conductor is secured, e.g., welded, to the second material sample. All electrical connections are insulated from the autoclave. The distance between the two material samples is kept small, typically one to three millimeters.

The autoclave is then heated to a predetermined temperature, and under the preselected conditions, the cross head moves upward relative to the support plate. Since the support plate is substantially stationary, the first material sample also is substantially stationary. Such upward movement of the cross head therefore results in a tensile stress being placed on the first material sample. The second material sample is not subjected to such stress.

As the first material sample is subjected to tensile stress, the strain induced differential potential signal remains substantially unchanged until cracking begins to occur in the first material sample. When such cracking begins to occur, bare metal surface begins to expose causing rapid electrochemical reactions resulting in transients that can be observed in the strain induced differential potential signal. Therefore, such transients indicate at least the onset of stress corrosion cracking.

Using the test apparatus described above, the conditions under which stress corrosion cracking occurs can be readily and easily identified. In addition, such test apparatus potentially eliminates the timely process of having to shut-down test operations, remove the test samples, and perform examinations of such test samples to determine whether the samples exhibit the onset characteristics of stress corrosion cracking. Rather, with the subject test apparatus, the onset of stress corrosion cracking is easily and quickly identified by analyzing the strain induced differential potential signal.

DETAILED DESCRIPTION OF THE DRAWINGS

Generally, the onset of stress corrosion cracking has been identified in the past by performing microscopic examination of material samples. Of course, in order to perform such examination, the material sample to be inspected must be removed and located within a suitable environment for examination. In a nuclear reactor, for example, this means that a material sample must be removed, or cut out of, a larger section of the material, and then shipped to a lab for examination. This process is time consuming and possibly subject to human error since microcracks during their initiation may not be detectable under microscopic examination.

It has been found that in addition to cracking characteristics that are observable using microscopic examination, during the onset of stress corrosion cracking, materials exhibit a potential change due to rapid electrochemical reaction occurring on the bare surfaces generated by cracking. By monitoring a sample to detect any such potential change, e.g., relative to a selected reference, it is possible to identify the onset of cracking without requiring that a sample be cut-out, removed and subjected to microscopic examination.

Figure 1:
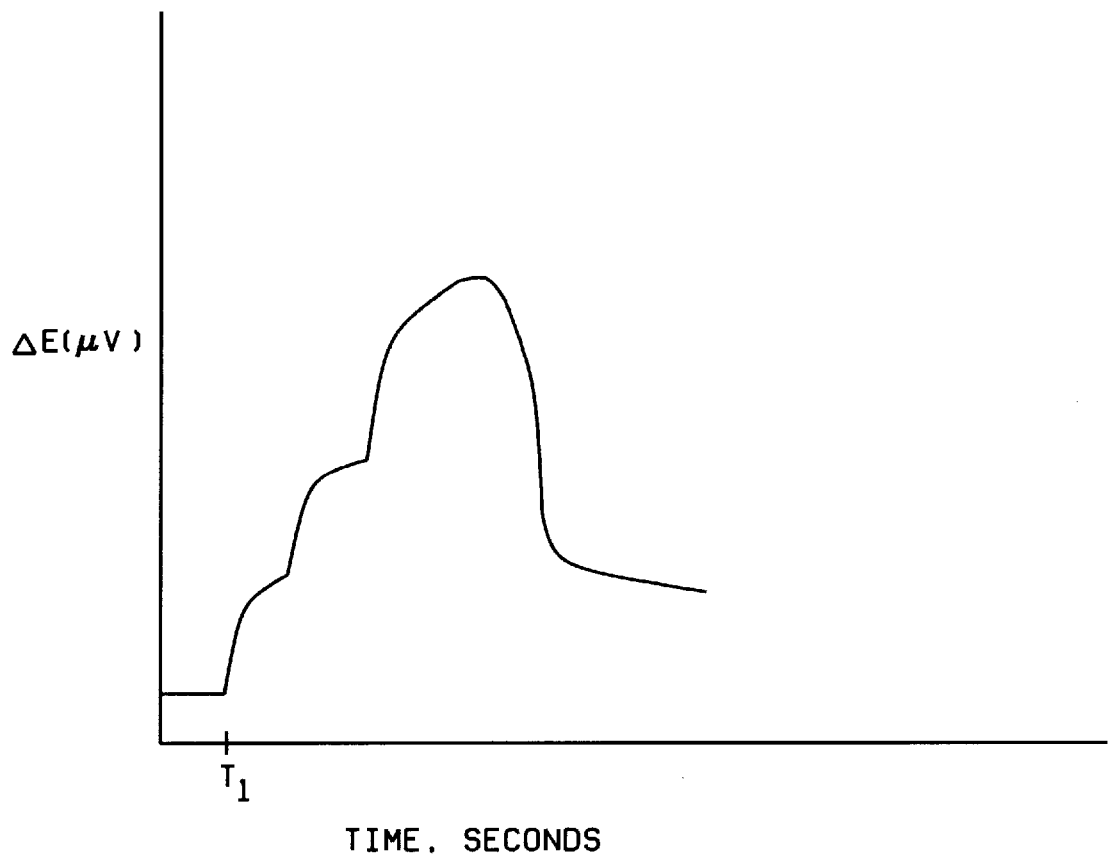
FIG. 1 is a chart illustrating the differential potential measured between stressed and unstressed samples versus time as the applied tensile stress is increased for the stressed sample.

As an example of the transients observed during crack initiation, FIG. 1 is a chart illustrating strain induced potential change, $\Delta E$ in microvolts, versus time. More specifically, the potential of a stressed material sample and an unstressed material sample can be measured and compared. The strain induced differential potential signal represents the potential difference of the stressed material sample as compared to the unstressed material sample. When no cracking is present, the differential potential signal is believed to remain substantially unchanged. When cracking initiates, however, transients are present in the strain induced differential signal as represented in FIG. 1 starting at a time $T_1$.

Figure 2:
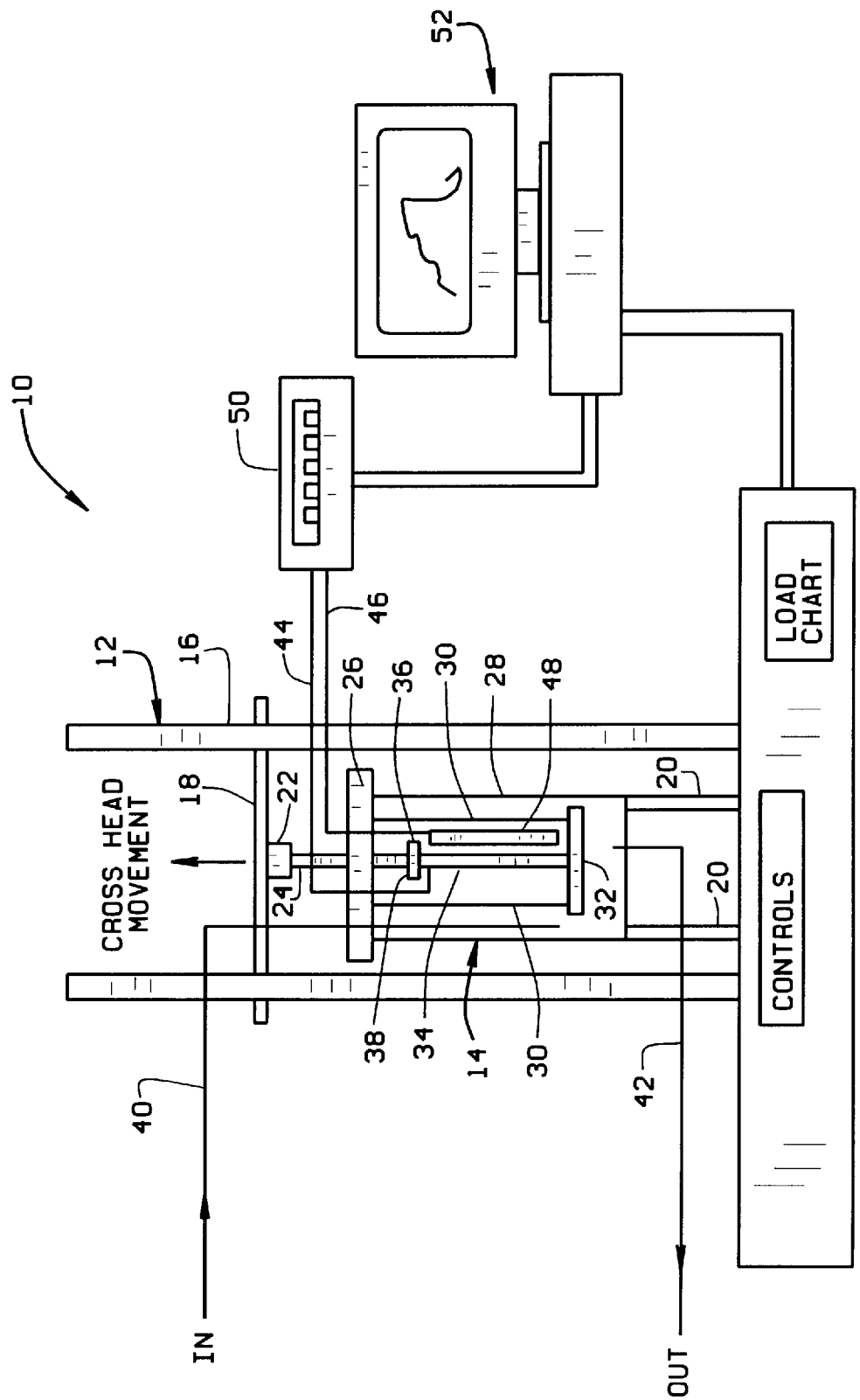
FIG. 2 is a schematic illustration of a laboratory stress corrosion cracking test apparatus in accordance with one embodiment of the present invention.

In one aspect, the present invention is a test apparatus which, using the principles described above, detects the onset of stress corrosion cracking. More specifically, FIG. 2 is a schematic, partial cross section, illustration of a stress corrosion cracking test apparatus 10 in accordance with one embodiment of the present invention. Apparatus 10 includes a materials straining apparatus 12 and an autoclave 14. Straining apparatus 12 includes a rotatable (corkscrew type motion), substantially cylindrical member 16 having a helical slot (not shown) formed therein, and a cross head 18. Autoclave 14 is supported within cylindrical member 16 on autoclave leg supports 20. Autoclave 14 is fully insulated to maintain temperature. Cross head 18 is positioned at least partially within rotatable member 16 and extends through the helical slot in member 16. A load cell 22 is connected to cross head 18, and a pull rod 24 is connected to load cell 22. Straining apparatus 12 may, for example, be the straining apparatus known as the Instron Universal Testing Instrument Model 1130, commercially available from Instron Corporation, Massachusetts, U.S.A.

Autoclave 14 has a head portion 26 and a substantially cylindrical main body portion 28. Support rods 30 extend from autoclave head portion 26 to a support plate 32 which is insulated from support rods 30 using ceramic discs (not shown) at the interfaces of support rods 30 and plate 32. Support plate 32 is positioned within autoclave 14, and support plate 32 is configured to engage a first material sample 34. Specifically, a ceramic pin (not shown) extends through support plate 32 and into sample 34. Sample 34 also is coupled to pull rod 24 by an insulated coupling 36. Coupling 36, in one embodiment, includes a sleeve 38 (sometimes referred to as an open cylinder 38) that, at one end, threadedly engages with pull rod 24, and at its other end, has a pair of opposed, aligned openings (not shown). A ceramic pin (not shown) extends through the aligned openings in open cylinder 38 and an opening (not shown) in sample 34.

An inlet water tube 40 extends from an external pool of water (not shown), through head portion 26 and into main body portion 28. An outlet water tube 42 extends through main body portion and to the external pool of water.

Apparatus 10 further includes a first electrical conductor 44 for being electrically connected to first material sample 34, and a second electrical conductor 46 for being electrically connected to a second material sample 48. Pull rod 24, tubes 40 and 42, and electrical conductors 44 and 46 extend into autoclave 14 through respective insulated fittings. An electrometer 50 is electrically connected to first and second electrical conductors 44 and 46, and electrometer 50 is configured to generate a strain induced differential potential signal representative of a difference in potential between first sample 34 and second sample 48. A computer 52 is connected to receive the output of electrometer 50 and the output of load cell 22.

Prior to operation, first material sample 34 is located in autoclave 14 and connected to and between straining apparatus coupling 36 and support plate 32 as described above. One end of first electrical conductor 44 is secured, e.g., welded, to first material sample 34. Second material sample 48 also is located in autoclave 14 and is supported within autoclave 14 by second electrical conductor 46. Specifically, one end of second electrical conductor 46 is secured, e.g., welded, to second material sample 48. All electrical conductors are kept insulated from autoclave 14.

Autoclave 14 is then heated to a predetermined temperature by controlling the temperature of water supplied to autoclave 14 via inlet water tube 40. Once the conditions within autoclave 14 have satisfied some predetermined criteria, rotatable member 16 of straining apparatus 12 is rotated so that cross head 18 moves upward relative to support plate 32. Since support plate 32 is substantially stationary, and since first material sample 34 is secured to support plate 32 and is coupled to cross head 18, a tensile stress is placed on first sample 34 as cross head 18 moves upward. Second material sample 48, kept within one to three millimeters of first material sample 34, is not subjected to such stress and remains substantially unstressed. The potential of both samples 34 and 48 is monitored by electrometer 50, and electrometer 50 generates a strain induced differential potential signal representative of the potential difference between first sample 34 and second sample 48.

Even as first material sample 34 is subjected to tensile stress, and until the initiation of cracking in first sample 34, the strain induced differential potential signal remains substantially unchanged. Once cracking is initiated, however, bare surface is exposed and transients will be observed in the strain induced differential potential signal. Such transients indicate at least the onset of stress corrosion cracking in first sample 34.

Using test apparatus 10 described above, the conditions under which stress corrosion cracking occurs can be readily and easily identified. In addition, test apparatus 10 potentially eliminates the timely process of having to shut-down test operations, remove sample 34, and perform examination of sample 34 to determine whether sample 34 exhibits the onset characteristics of stress corrosion cracking. Rather, with test apparatus 10, the onset of stress corrosion cracking is easily and quickly identified by analyzing the strain induced differential potential signal.

It is contemplated that in using test apparatus 10, and in one embodiment, straining apparatus 12 would be operated to strain first sample 34 at a constant extension rate of, for example, 4.4×E−7/s. First and second electrical conductors 44 and 46 are 1/16" stainless steel wire which are led through respective insulated fittings (not shown) in autoclave 14. Ideally, before straining first sample 34, the strain induced differential potential ΔE should be zero. However, due to non-homogeneity of the sample surfaces, a non-zero ΔE is generally observed. When first sample 34 is strained at a constant extension rate, any change in strain induced differential potential ΔE is related to the differences between strained (first) and unstrained (second) samples 34 and 48.

The value of ΔE generally increases as a result of the film rupture and repassivation processes taking place on strained sample 34. A most significant difference is observed when intergranular stress corrosion (IGSCC) cracking initiates on the surface of first sample. As this happens, strain induced differential potential ΔE values typically will have multiple transient behavior consistent with the film rupture/repassivation model for IGSCC cracking. These transients continue until cracking propagates to such an extent that the base line potential masks the ΔE transients. The appearance of these transients signals the initiation of stress corrosion cracks. Thus, this approach is an excellent method of detecting, in-situ, the initiation of stress corrosion cracks.

Test apparatus 10 is believed to be useful for both low and high temperature environments. In addition, test apparatus 10 uses only the ΔE measurement and does not require the use of reference electrodes. The ΔE measurement can be made using electrometer 50 with its output connected either to a sensitive recorder or computer 52 via an appropriate interface, so that the transient data can be recorded in real time. The amplitude of the transients and the frequency can be used to relate to the repassivation and film rupture rates during the process of crack initiation. In addition, a zero resistance ammeter can be used in place of electrometer 50 and the strain induced differential current ΔI can be monitored which gives kinetic information on the cracking and repassivation processes.

Figure 3:
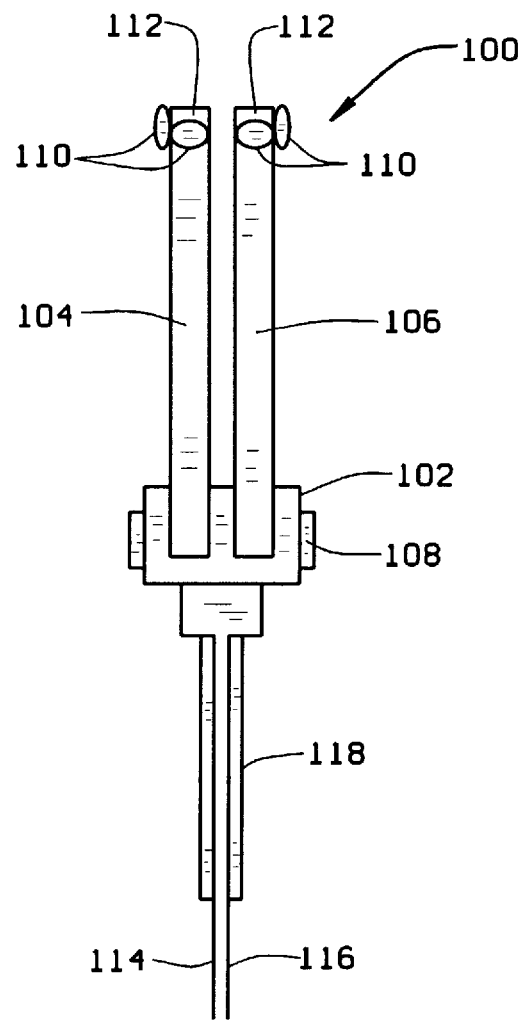
FIG. 3 is a schematic illustration of a passive stress corrosion cracking detector in accordance with one embodiment of the present invention.

FIG. 3 is a schematic illustration of a passive stress corrosion cracking detector 100 in accordance with one embodiment of the present invention. Detector 100 includes a ceramic insulator mounting member 102. A first material sample 104 and a second material sample 106 are secured to mounting member 102. A metal bolt 108 extends through an insulting sleeve (not shown) and through first and second material samples 104 and 106 and secures samples 104 and 106 to mounting member 102. First material sample 104 is cold worked and second material sample 106 is not cold worked. First material sample 104 can be cold worked, for example, by rolling, forging, and machining operations, or by subjecting sample 104 to a tensile stress.

Ceramic buttons 110 are shown as being located at upper ends 112 of samples 104 and 106. Ceramic buttons 110 are used to isolate samples 104 and 106 from a housing, such as a local power range monitor (LPRM) housing of a boiling water reactor (BWR, not shown). Specifically, samples 104 and 106 could be located within an LPRM housing to protect samples 104 and 106 from direct contact with other components of the nuclear reactor. Such an LPRM construction could be used for crack detection in the core region and in the lower plenum of a BWR. Also, for detection of cracking in the lower plenum, detector 100 could be located in a drain line flange. If recirculation pipe crack detection is to be performed, then detector 100 could be placed in a recirculation pipe decon flange. Of course, many other types of housing and enclosures can be used depending on the particular environment in which cracking is to be detected.

A first electrical conductor 114 is electrically connected to first material sample 104 and a second electrical conductor 116 is electrically connected to second material sample 106. Conductors 114 and 116 may be located within an insulator 118. An electrometer (not shown) is electrically connected to first and second electrical conductors 114 and 116, and the electrometer is configured to generate a strain induced differential potential signal representative of a difference in potential between first sample 104 and the second sample 106.

To detect the possible onset of cracking in a reactor, detector 100 is located within the reactor at the location where monitoring is desired. First sample 104 is preferably cold worked to induce residual stresses typical of welds at that location. During the reactor operation, the strain induced differential potential signal of first and second samples 104 and 106 is monitored. If the strain induced differential potential signal remains substantially unchanged during reactor operation, then at least at the location of detector 100, this condition indicates that no cracking is initiating or occurring under the residual stress conditions seen by sample 104. If, however, the strain induced differential potential signal changes during reactor operation, e.g., transients are present, this condition indicates that at the location of detector 100, an inspection should be performed at the next outage to determine whether cracking is occurring. In addition to, or rather than, measuring the strain induced differential potential signal ΔE, the strain induced differential current signal ΔI can also, or alternatively, be monitored by replacing electrometer 50 with a zero resistance ammeter.

Detector 100 provides the advantage of facilitating early identification of crack initiation. Detector 100 provides this important advantage in-situ and without necessarily requiring, for every inspection, removal of a material sample and subjecting the sample to microscopic examination. Specifically, with detector 100, and if no transients are observed in the monitored strain induced differential potential signal, there is no detector indication that sample removal and inspection is required, although such removal and inspection may be performed due to other circumstances.

Detector 100 is sometimes referred to herein as being "passive" in that no tensile stresses are directly applied to first material sample 104 except for the residual stress generated by the cold work. The present invention also includes, in another aspect, active detectors in which tensile stresses are directly applied to the first material sample as shown in FIG. 4.

Figure 4:
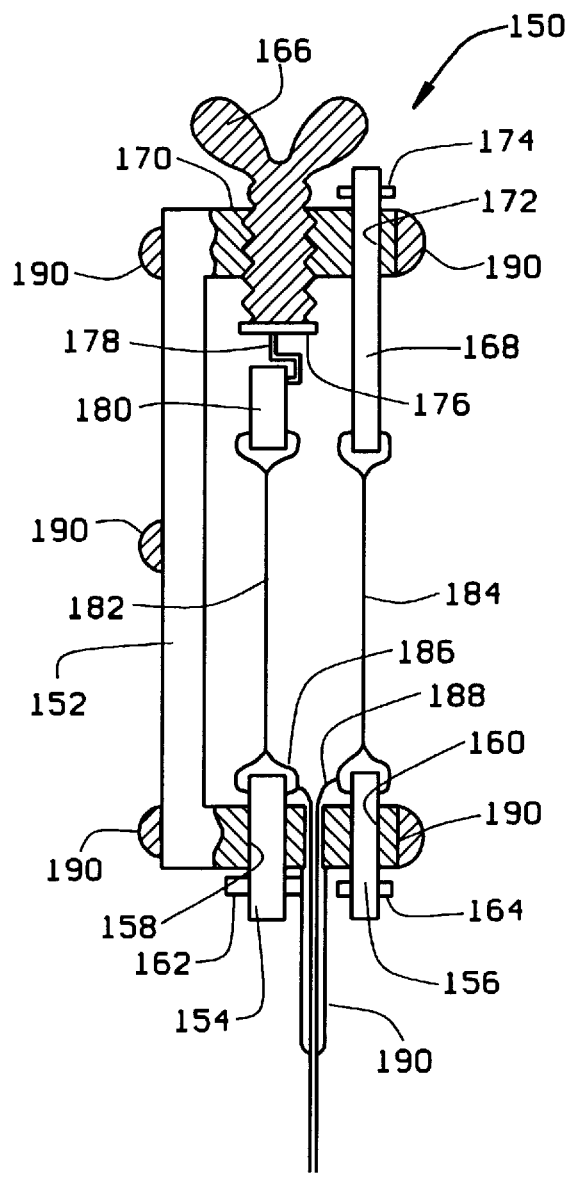
FIG. 4 is a partial cross section illustration of an active stress corrosion cracking detector in accordance with one embodiment of the present invention.

More specifically, FIG. 4 is a partial cross section illustration of an active stress corrosion cracking detector 150 in accordance with one embodiment of the present invention. Detector 150 includes a metal "C" clamp 152. First and second ceramic support cylinders 154 and 156 extend through openings 158 and 160 in clamp 152 and are held in place by ceramic pins 162 and 164, respectively. A butterfly nut 166 and a ceramic rod 168 extend through openings 170 and 172 in clamp 152. Rod 168 is held in place by ceramic pin 174 Nut 166 is threadedly engaged to clamp 152, and a ball bearing 176 is sealed to nut 166. Metal hook 178 is secured to bearing 176, and nut 166 is rotatable relative to hook 178. Hook 178 extends through, and supports, a third ceramic support cylinder 180.

A first wire specimen 182 is engaged to third cylinder 180 and first cylinder 154. A second wire specimen 184 is engaged to ceramic rod 168 and second cylinder 156. Specifically, first wire specimen 182 is configured to extend through openings (not shown) in cylinders 180 and 154. Similarly, second wire specimen 184 is configured to extend through openings (not shown) in rod 168 and cylinder 156. Wire specimens 182 and 184 are electrically connected to leads 186 and 188, respectively, which extend through an insulator 190. Ceramic buttons 190 are provided to insulate detector 150 from a housing (not shown).

Prior to performing detection, nut 166 is adjusted so that the desired tensile stress is placed on first specimen 182. Second specimen 184 has substantially no tensile stress placed thereon. Detector 150 is then located in a desired location for crack detection. For example, to detect the possible onset of cracking in a reactor, detector 150 is located within the reactor at the location where monitoring is desired. During the reactor operation, the strain induced differential potential, or current, signal of first and second samples 182 and 184 is monitored. If the strain induced differential potential signal remains substantially unchanged during reactor operation, then at least at the location of detector 150, this condition indicates that no cracking is initiating or occurring under the tensile stress conditions seen by sample 182. If, however, the strain induced differential potential signal changes during reactor operation, e.g., transients are present, this condition indicates that at the location of detector 150, an inspection should be performed at the next outage to determine whether cracking is occurring.

In addition to providing the advantages of detector 100, detector 150 provides the advantage that tensile stresses are applied to sample 182 instead of the cold work applied to first sample 104 in detector 100. Such applied stresses may facilitate more accurate crack detection since first sample 182 is subjected to tensile stresses at the same time it is exposed to the corrosive environment.

Figure 5:
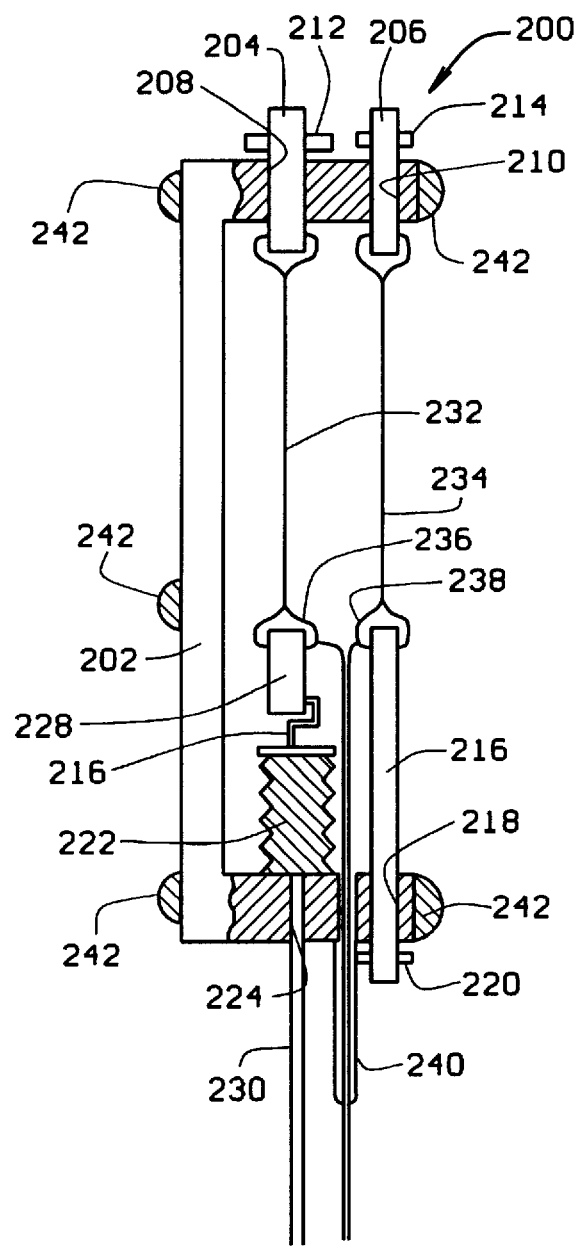
FIG. 5 is a partial cross section illustration of an active stress corrosion cracking detector in accordance with another embodiment of the present invention.

FIG. 5 is a partial cross section illustration of an active stress corrosion cracking detector 200 in accordance with another embodiment of the present invention. Detector 200, as described hereinafter in more detail, provides the advantage that the tensile stress applied can be adjusted during detector operation. More specifically, detector 200 includes a metal "C" clamp 202. First and second ceramic support cylinders 204 and 206 extend through openings 208 and 210 in clamp 202 and are held in place by ceramic pins 212 and 214, respectively. A ceramic rod 216 extends through an opening 218 in clamp 202. Rod 216 is held in place by ceramic pin 220. A metallic bellows 222, or piston (not shown), is secured to clamp 202 and in alignment with an air channel 224 through clamp 202. A metal hook 226 is secured to bellows 222, and hook 226 extends through, and supports, a ceramic support cylinder 228. A metal capillary tube 230 extends from clamp 202 to a liquid or gas pressure source (not shown).

A first wire specimen 232 is engaged to cylinder 204 and cylinder 228. A second wire specimen 234 is engaged to cylinder 206 and ceramic rod 216. Specifically, first wire specimen 232 is configured to extend through openings (not shown) in cylinders 204 and 228. Similarly, second wire specimen 234 is configured to extend through openings (not shown) in cylinder 206 and rod 216. Wire specimens 232 and 234 are electrically connected to leads 236 and 238, respectively, which extend through an insulator 240. Ceramic buttons 242 are provided to insulate detector 200 from a housing (not shown).

Prior to performing detection, a selected pressure is applied to cause bellows 222 to expand or contract. Such expansion and contraction of bellows 222 causes a desired tensile stress is placed on first specimen 232. Second specimen 234 has substantially no tensile stress placed thereon. Detector 200 is then located in a desired location for crack detection. For example, to detect the possible onset of cracking in a reactor, detector 200 is located within the reactor at the location where monitoring is desired. During the reactor operation, the strain induced differential potential, or current, signal of first and second samples 232 and 234 is monitored. If the strain induced differential potential signal remains substantially unchanged during reactor operation, then at least at the location of detector 200, this condition indicates that no cracking is initiating or occurring under the tensile stress conditions seen by sample 232. If, however, the strain induced differential potential signal changes during reactor operation, e.g., transients are present, this condition indicates that at the location of detector 200, an inspection should be performed at the next outage to determine whether cracking is occurring.

In addition to providing the advantages of detector 150, detector 200 provides the advantage that the tensile stresses applied to first sample 232 during detection operation can be adjusted. Specifically, the gas or liquid pressure supplied to bellows 222 can be adjusted during detection operations and therefore, the tensile stress of first sample 232 can also be adjusted.

From the preceding description of the present invention, it is evident that the objects of the invention are attained. Although the invention has been described and illustrated in detail, it is to be clearly understood that the same is intended by way of illustration and example only and is not be taken by way of limitation. Accordingly, the spirit and scope of the invention are to be limited only by the terms of the appended claims.

What is claimed is:

1. A detector for detecting stress corrosion crack initiation in a corrosive environment, said detector comprising:
    a ceramic insulator mounting member;
    a first material sample secured to said mounting member, said first material sample having been cold worked to have residual tensile stress;
    a second material sample secured to said mounting member adjacent said first material sample, said second material sample not having any substantial residual tensile stress;
    a first electrical conductor electrically connected to said first material sample;
    a second electrical conductor electrically connected to said second material sample; and
    an electrical monitoring device configured to generate a strain induced differential signal.

2. A detector in accordance with claim 1 further comprising a metal bolt positioned within an insulating sleeve, said metal bolt extending through said first and second material samples and securing said samples to said mounting member.

3. A detector in accordance with claim 1 wherein said electrical monitoring device comprises:
    an electrometer electrically connected to said first and second electrical conductors, said electrometer configured to generate a strain induced differential potential signal representative of a difference in potential between said first sample and said second sample.

4. A detector in accordance with claim 1 wherein said electrical monitoring device comprises:
    a zero resistance ammeter electrically connected to said first and second electrical conductors, said ammeter configured to generate a strain induced differential current signal representative of a difference in current in said first sample and said second sample.

5. A detector in accordance with claim 1 wherein said first material sample has been cold worked by rolling.

6. A detector in accordance with claim 1 wherein said first material sample has been cold worked by forging.

7. A detector in accordance with claim 1 wherein said first material sample has been cold worked by machining.

8. A detector in accordance with claim 1 wherein said first material sample has been subjected to tensile stress.

9. Apparatus for testing a specimen to detect the onset of stress corrosion cracking, said apparatus comprising:
    a straining apparatus comprising a cross head and a pull rod coupled to said cross head;
    an autoclave positioned below said cross head;
    a first electrical conductor for being electrically connected to a first material sample;
    a second electrical conductor for being electrically connected to a second material sample; and
    an electrical monitoring device configured to generate a strain induced differential signal.

10. Apparatus in accordance with claim 9 wherein said straining apparatus further comprises a rotatable, substantially cylindrical member having a helical slot formed therein, said cross head positioned at least partially within said rotatable member and extending through said slot so that as said rotatable member rotates, said cross head moves relative to said autoclave.

11. Apparatus in accordance with claim 10 wherein said straining apparatus further comprises a support plate positioned within said autoclave, said support plate configured to engage a first material sample.

12. Apparatus in accordance with claim 11 wherein said autoclave comprises a head portion and a substantially cylindrical main body portion, and said straining apparatus further comprising support rods extending from said head portion to said support plate, and ceramic discs insulating said support plate from said support rods.

13. Apparatus in accordance with claim 9 wherein said straining apparatus further comprises a load cell for sensing load on the first material sample.

14. Apparatus in accordance with claim 9 wherein said electrical monitoring device comprises:
    an electrometer electrically connected to said first and second electrical conductors, said electrometer configured to generate a strain induced differential potential signal representative of a difference in potential between said first sample and said second sample.

15. Apparatus in accordance with claim 9 wherein said electrical monitoring device comprises:
    an ammeter electrically connected to said first and second electrical conductors, said ammeter configured to generate a strain induced differential current signal representative of a difference in current in said first sample and said second sample.

* * * * *